United States Patent

Matsuhisa et al.

[11] Patent Number: 5,824,474
[45] Date of Patent: Oct. 20, 1998

[54] METHOD FOR DETECTING NUCLEIC ACID

[75] Inventors: Akio Matsuhisa, Osaka; Kiyotaka Shiba, Tokyo, both of Japan; Yoshikazu Mikawa, San Diego, Calif.; Yuichiro Kishi, Wakayama, Japan

[73] Assignee: Fuso Pharmaceutical Industries, Ltd., Osaka, Japan

[21] Appl. No.: 592,293

[22] PCT Filed: Aug. 10, 1993

[86] PCT No.: PCT/JP93/01124

§ 371 Date: Feb. 8, 1996

§ 102(e) Date: Feb. 8, 1996

[87] PCT Pub. No.: WO95/04832

PCT Pub. Date: Feb. 16, 1996

[51] Int. Cl.⁶ .............................. C12Q 1/68; C07H 21/02; C07H 21/04
[52] U.S. Cl. ............................. 435/6; 536/23.1; 536/24.3
[58] Field of Search ................................ 435/6; 536/23.1, 536/24.3; 935/76, 77, 78

[56] References Cited

U.S. PATENT DOCUMENTS 4,556,653  12/1985  Paau et al. .............................. 436/501
5,053,326  10/1991  Renz ............................................ 435/6
5,599,667   2/1997  Arnold, Jr., et al. ........................ 435/6

OTHER PUBLICATIONS

Davis et al. Basic Methods in Molecular Biology. pp. 59–78 Elsvier Publishing, NY (1986).

The Stratagene Catalog p. 39 (1988 Edition).

Schmid et al. Location of Spermine and other polyamines on DNA as revealed by photoaffinity cleavage with polyaminobenziazonium salts. Biochemistry 30 :4357–4361 (1991).

*Primary Examiner*—W. Gary Jones
*Assistant Examiner*—Ethan Whisenant

[57] ABSTRACT

A method of detecting a nucleic acid which comprises bringing a solid carrier suspected to carry or contain a nucleic acid into contact with a polyamine to which a label capable of generating a detectable signal or a precursor thereof is bound, to form a complex between said nucleic acid and said polyamine, said precursor converting into said label, if used, removing the polyamine which has not formed any complex before or after the conversion of said precursor and then detecting said label.

27 Claims, 8 Drawing Sheets

METHOD FOR DETECTING NUCLEIC ACID

FIELD OF THE INVENTION

The present invention relates to a method of detecting a nucleic acid employing the property of nucleic acids that polyamines bind thereto.

DESCRIPTION OF THE PRIOR ART

As a conventional method of detection of nucleic acids, methods using ethidium bromide have been widely adopted. The known method comprises intercalation of ethidium bromide into a nucleic acid so as to emit fluorescence by which a location of a nucleic acid is detected. However, the known method is very inconvenient because fluorescence cannot be detected in the light and the locations of nucleic acids can be detected only by corresponding original gel to a photograph thereof which were taken under ultraviolet radiation in the dark. And also, ethidium bromide requires careful handling because of its strong carcinogenic property (cf. Gene Operation Manual, page 2, lines 18–21, Kodansha Scientific Press). Alternatively, methods using anionic gold colloid and cationic iron colloid cacodylate are also known (Gene Anal. Techn. pages 1 to 5, 1986), however, the sensitivity of the methods is low. In addition, since the method using gold colloid is a kind of background staining system, detection of a nucleic acid is not easy and also hybridization after the staining is disadvantageously affected. In the method using iron colloid, there is a disadvantage that staining after hybridization cannot be carried out. The development of an operably easy, safe, simple and reproducible method for detecting a nucleic acid has been expected for a long time. It is already known that a polyamine can bind to DNA and also has affinity for RNA (cf. Biochemical Journal, 123, 811–815 (1967), Journal of Molecular Biology, 24, 113–122 (1967), ibid., 42, 363–373 (1969) and ibid., 121, 327–337 (1987)). And also, in order to detect target polynucleotides, it is known to use probes which bond covalently to polynucleotide complementary to protein modified with polyamine (Japanese Patent Publication (in Japanese) A: TOKUKOHYOSHO 60-501488 (1985), to which corresponds, Japanese Patent Publication B: TOKUKOHEI 2-59720 (1990) and its divisional application, Japanese Patent Publication A: TOKUKAIHEI 1-124400 (1989)). However, no method of detecting a nucleic acid is known which comprises forming a complex of a labeled polyamine and a nucleic acid.

SUMMARY OF THE INVENTION

The object of the present invention is thus to provide (1) a method of detecting a nucleic acid which comprises bringing a solid carrier suspected to carry or contain a nucleic acid into contact with a polyamine to which a label capable of generating a detectable signal or a precursor thereof is bound, to form an electrostatically bonded complex between said nucleic acid and said polyamine, said precursor converting into said label, if used, removing the polyamine which has not formed any electrostatically bonded complex before or after the conversion of said precursor and then detecting said label, and (2) a method of differentiating a target nucleic acid from any nucleic acid other than said target nucleic acid which comprises combining the following steps (i) and (ii) in voluntary order:

(i) A step which comprises bringing a solid carrier suspected to carry or contain a target nucleic acid, into contact with a probe to which a label capable of generating a detectable signal or a precursor thereof is bound, being capable of hybridizing with said target nucleic acid under hybridization conditions, to form a hybrid, said precursor converting into said label, if used, removing said probe which has not formed any hybrid before or after the conversion of said precursor and then detecting said label, and (ii) another step which comprises bringing a solid carrier suspected to carry or contain a target nucleic acid, into contact with a polyamine to which a label capable of generating a detectable signal or a precursor thereof is bound, to form an electrostatically bonded complex between said nucleic acid and said polyamine, said precursor converting into said label, if used, removing said polyamine which has not formed any electrostatically bonded complex before or after the conversion of said precursor and then detecting said label, and (3) A kit for detecting a nucleic acid comprising (i) a enzyme-labeled polyamine (ii) a chromogen which generates a label by enzymatic action.

The terms used herein are illustrated as follows:

The term "a nucleic acid" means a polymer in which nucleotides consisting of a purine or pyrimidine base, a pentose and phosphoric acid as a basic unit are polymerized by ester linkages of the phosphoric acids. As a base, there are included adenine, cytosine, guanine, thymine and uracil, and modified bases thereof. Nucleic acids are distinguished by a sugar moiety into DNA and RNA, by the number of strands into single and double stranded nucleic acids and also by steric structure.

As a "solid carrier", there may be exemplified a thin plate, a sheet, a strip, a slab, film, membrane, etc. There are typically mentioned agarose gel, nylon membrane, filter paper, nitrocellulose membrane, etc.

The term "a label" means a substance which generates measurable signal and includes an enzyme (in corporation with a substrate), a spin compound, a radioactive nuclear atom, a fluorescent substance, a chemiluminescent substance, an absorption substance, etc, and an enzyme is preferred. As the enzyme there may be included peroxidase, β-galactosidase, glucose oxidase, alkaline phosphatase, glucose-6-phosphate dehydrogenase, etc. As a method for determination of enzyme activity, there may be mentioned absorption method, fluorescence method and chemiluminescence method. For example, in the absorption method, peroxidase is used in cooperation with a chromogen, such as 2,2'-azinodi(3-ethylbenzthiazolin)-6'-sulfonate (ABTS) and the color developed is measured by the absorption method. Glucose oxidase produces hydrogen peroxide from glucose as a substrate and therefore, it can be determined by the same way as above by conjugating with peroxidase. β-galactosidase can be determined using o-nitrophenyl-β-D-galactoside as a substrate. In the fluorescence method, for example, peroxidase can be determined using p-hydroxyphenylpropionic acid as a substrate, β-galactosidase can be determined using fluorescein-β-galactosidase or 4-methylunbelliferyl-β-D-galactoside as a substrate and phosphatase can be measured using unbelliferyl phosphate or bromochloroindolyl phosphate/nitroblue-tetrazolium as a substrate. In the chemiluminescence method, for example, peroxidase can be measured using luminol and hydrogen peroxide as substrates. A label (e.g. an enzyme) may be bound to a polyamine by a crosslinking agent such as benzoquinone (quinhydrone), bis[2-(succinimidocarbonyloxy)ethyl]sulfon (BSOCOES), bis(sulfosuccinimidyl)-suberate (BS3), 1,2-difuluoro-2,4-dinitrobenzene (DFDNB), 4,4'-diisothiocyano-2,2'-disulfostilbene disodium salt (CDIDS), dimethyl adipin-imidate dihydrochloride, N-(γ-maleimidobutyryloxy) succnimide (GMBS), N-(4-azidophenylthio)phthalimide (APTP), N-succinimidyl-6-(4'-azido-phenyl)-1,3'-dithiopropionate (SADP), pyridine disulfide, thiophthalimide, etc.

The term "a precursor of a label" means, for example, a label blocked with a blocking substance, which can be converted into the detectable label.

The term "signal" means visible ray, fluorescence, radioactive ray, or other electromagnetic waves and the like. A measured value of signal is to be related to an amount of a substance which emits the signal.

The term "detecting a label" is to detect a signal by physical or technical means.

The term "polyamine" herein means a compound which has aliphatic backbone having 2 or more primary amino groups includes naturally occurring (a living body) amines and synthetic polymers. In general, primary amino groups are at both ends of a chain of 3 to 50 carbon atoms, preferably, about 6 to about 15 or about 20 carbon atoms, and the chain may be interrupted by one or more imino groups. As a typical naturally occurring polyamine, there may be included 1,3-diaminopropane, putrescine, cadaverine, norspermidine, spermidine, homospermidine, aminopropylcadaverine, telmine, spermine, thermospermine, canavalmine, aminopentylnorspermidine, N,N'-bis(aminopropyl)cadaverine, caldopentamine, homocaldopentamine, caldohexamine, etc. A typical synthetic polyamine incrudes diethylenetriamine, triethylenetetramine, tetraethylenepentamine, pentaethylenehexamine, hexamethylenediamine, polyethyleneimine (an average molcular weight is about 10,000–about 200,000, preferably, about 20,000–about 100,000, for example, about 50,000–about 60,000, e.g. Polymin G 35 by BASF AG), etc.

The word "complex" (a verb) or "complex" (a noun) means to bond electrostatically and/or physically or a electrostatically and/or physically bonded product and does not mean to bond covalently or a covalently bonded product. "Complex" is generally reversible, and can be easily dissociated.

The term "hybridize" or "hybridization" means that, when two single-stranded polynucleotides are complementary or almost complementary (for example, more than 70%, preferably, more than 80 or 85%, especially, more than 90 or 95%), they bind to form a double-stranded polynucleotide. "Under hybridization conditions" means the conditions under which polynucleotides capable of hybridizing can produce a hybrid. In general, the conditions means that a temperature is below about 70° C., preferably below about 60° C., generally below about 40° to 55° C. and a period is short enough for hybridization.

"Target" presents a subject to be interested.

"Probe" is a DNA which is highly complementary to the target DNA and a part thereof and, in general, is shorter than the target DNA and has about 5–about 50 bases, preferably about 10–about 40 bases, for example, about 20–about 30 bases.

DETAILED DESCRIPTION OF PREFERRED EMBODIMENTS

Figure 1:
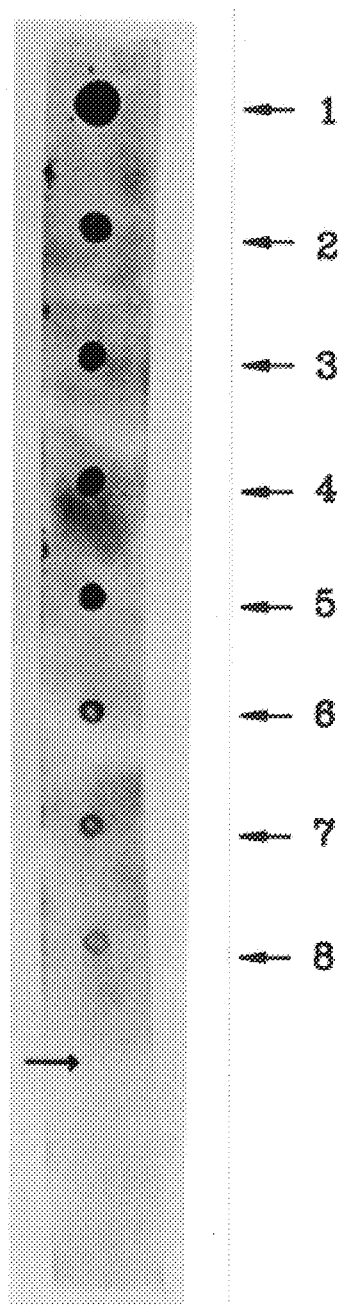
FIG. 1 shows the result of detection of λDNA in Example 1.

A typical method of detecting a nucleic acid according to the invention may be summarized as follows:

In an example of a complex consisting of a polyamine and an enzyme using benzoquinone, the reaction is considered to proceed according to the following scheme.

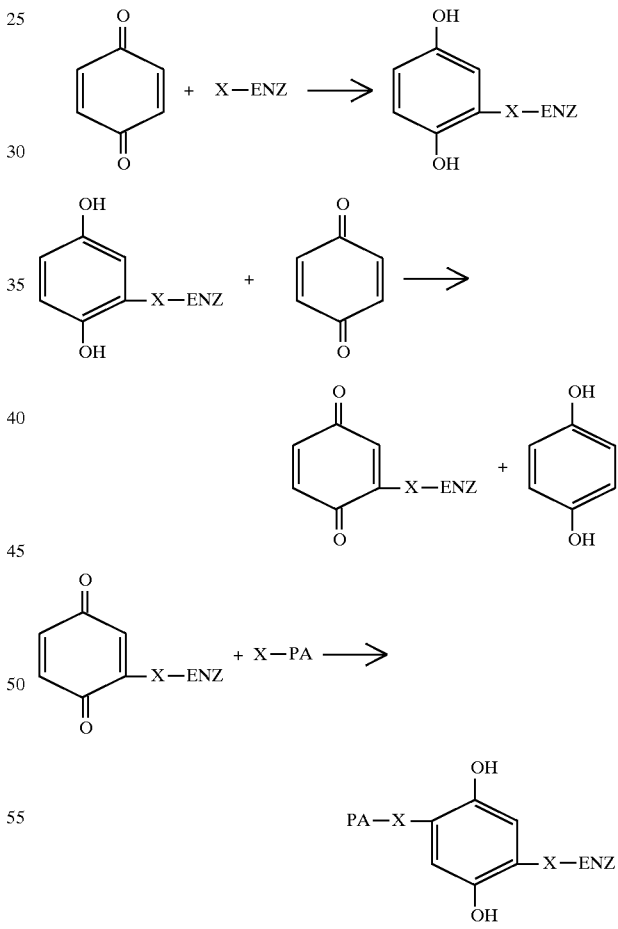

in which ENZ represents a residue from deletion of an amino group from an enzyme; PA represents a residue from deletion of an amino group from a polyamine; X represents a primary amine or a secondary amine.

The reaction is, for example, carried out as follows: To benzoquinone (about 1 part) is added an enzyme (about 150 parts) which has been previously purified, for example, by such means as dialysis, and preferably at a somewhat elevated temperature to give a reaction mixture of wine-red color, which was subjected to such a method as gel permeation chromatography and fractionated into purple, an yellow and wine-red fractions. The wine-red fraction is reacted with a polyamine (one of several parts of the enzyme) in the presence of a weak base while heating slightly to give an enzyme labeled-polyamine after suitable purification.

Detection of a nucleic acid is for example performed as follows:

(a) A nucleic acid specimen is dot-spotted on a membrane or is electrotransferred to a membrane after subjecting to gel electrophoresis and then the membrane is fixed by baking. After the membrane is treated with bovine serum albumin in a buffer, a labeled polyamine or a label-precursor labeled polyamine is reacted therewith. After washing, the label is detected, if a label-precursor is used, the label-precursor is converted into the label, and the label is then detected.

(b) DNA fragments are subjected to agarose gel electrophoresis and then Southern blotting. After prehybridization with radiolabeled probes while heating, the DNA fragments are hybridized. After washing, the position of DNA is detected using an X-ray film. Then the DNA is reacted with a labeled or a precursor-labeled polyamine and then a product thereof is developed with a suitable system to detect.

(c) DNA fragments are fixed on a membrane by dot blotting or by Southern blotting after subjecting to agarose gel electrophoresis and after prehybridization, are hybridized with Bio-DNA probes. After washing and blocking, the resulting product is reacted with an enzyme-labeled streptavidin and after washing and preincubation, in addition, another enzyme-labeled polyamine is reacted therewith. After washing, the resultant hybrid is subjected to color developments for each enzyme to give two different color patterns corresponding to hybridized DNA and non-hybridized DNA. For example, alkaline phosphatase/BCIP-NBT and peroxidase/DAB systems are developed into purple and brown, respectively. In such a method, the order of treatments with a probe and a polyamine may be reversible.

Such membrane as treated above is developing color in itself, but not as an X-ray film and therefore, a subject nucleic acid can be directly detected on the membrane. In addition, in PCR method, amplification products having similar molecular weights, but having different sequences, can be distinguished from each other by hybridization.

The method of detecting a nucleic acid according to the invention has the following advantages:

The method requires no dangerous reagents and can result in high sensitivity (i.e. picogram order in DNA and 10 picogram order in RNA). And also operation in the method is very easy, and if the reagents to be used in the method are incorporated into a kit, it becomes easier.

EXAMPLES

The present invention is illustrated by the following specific embodiments.

Example 1

Production of peroxidase- or alkaline phosphatase-labeled polyethyleneimine

Alkaline phosphatase (CIP, Boehringer-Mannheim GMbH, Grade 1), 0.81 ml/4.05 mg/7500 unit or horseradish peroxidase (Boehringer-Mannheim GMbH) is dialyzed against 0.1M phosphate buffer at 40° C. during one night and then, according to a method as described in Immuno Chemistry, Vol. 14, 767–774 (1977), is reacted with p-benzoquinone (120 µl/30 mg/ethanol) at 37° C. for 60 minutes in the dark. After subjecting to gel permeation chromatography on Sephadex G-25, wine-red fractions (2.7 ml) are taken up and 300 µl of 1M-NaHCO$_3$ (pH 9.0), 30 µl of polyethyleneimine (Epomin) were added thereto and fully mixed. The resultant mixture was reacted at 37° C. in the dark during one night, and then dialysed against 5 mM phosphate buffer (pH 6.8) to give an enzyme-polyethyleneimine conjugate, which was stable at 4° C. more than 1 year.

Nucleic acid blotting on membrane

Denatured λHind III DNA or *Escherichia coli* K-12 rRNA was dotblotted on a nylon membrane (Biodyne A, Pall Co. Ltd.) as described in "Molecular Cloning", 1982, Cold Spring Harbour Laboratory. Clone of *Staphylococcus aureus* genome DNA which was random-cloned into a vector pBR322 was amplified according to a method known to those skilled in the art, extracted and then split with Hind III. Specimens are fractionated by 1% agarose gel electrophoresis and the isolates were electroblotted on a membrane (40 V, for 4 hours). λHind III DNA is also blotted as above. The DNA or RNA specimen was subjected to baking (80° C., 2 hours) to fix on the membrane.

Detection of nucleic acid blotted on membrane

A membrane containing fixed DNA or RNA was soaked in 5 mM phosphate buffer-1% bovine serum albumin (BSA, Sigma, Fraction V), incubated at room temperature for 60 minutes and then was added alkaline phosphatase (or peroxidase)-labelled polyethyleneimine in a ratio of 100 µl/20 ml thereto and incubated at 37° C. for 120 minutes. The membrane was washed 3 times with 5 mM phosphate buffer-1% BSA-1% Tween 20 for 10 minutes and rinsed with 0.1M Tris HCl (pH 9.5)-10 mM-MgCl$_2$. The membrane was developed with 50 ml of a staining solution consisting of 0.1M Tris HCl (pH 9.5)-10 mM-MgCl$_2$ containing each 300 µl of bromochloroindolyl phosphate (BCIP: 75 mg/ml) and nitro blue tetrazolyium (NBT: 50 mg/ml).

Southern Blotting Hybridization

Nick translation reaction was performed using *Staphylococcus aureus* genome kbp fragment DNA according to a conventional technique with $^{32}$P-dCTP or Bio-11-dUTP (BRL) to prepare $^{32}$P-DNA or Bio-DNA. The membrane was treated for hybridization with hybridization buffer (5×SSC, 0.1% BSA, 0.1% Tween 20) containing denatured probes at 42°–55° C. during one night. Then the membrane was washed with 0.16×SSC-0.1% Tween 20 at 55° C. for 30 minutes (The endpoint of washing is referred to as "the point A").

When $^{32}$P-DNA probe was used, at the point A, the moist membrane was wrapped by polyethylene film and detected signal by exposing to an X-ray film. Then, the membrane was treated for blocking with 3% BSA-0.1% Tween 20-phosphate buffer saline (PBS) at 42° C. for more than 3 hours, followed by adding 0.1% BSA-0.1% Tween-PBS containing 100 µl of peroxidase-labelled polyethyleneimine pr sheet, the membrane was reacted for 2–3 hours. The membrane was washed 3 times for 20 minutes with 0.1% Tween 20-PBS and developed with a diaminobenzidine (DAB)-H$_2$O$_2$ system.

When Bio-DNA probe was used, after the point A, the membrane was treated with PBS-0.5% Tween 20 at room temperature for 60 minutes. After treatment with PBS-0.05% Tween 20 containing alkaline phosphatase-labeled streptavidine at room temperature for 20 minutes, the membrane was washed 2 times with PBS-0.5% Tween 20 for 10 minutes. After preincubation with PBS-0.1% BSA-0.1% Tween 20 at room temperature for 20 minutes, and addition of peroxidase-labeled polyethyleneimine thereto, the membrane was reacted at 42° C. for 3 hours. After the membrane was washed 3 times with PBS-0.1% Tween 20 for 10 minutes, it was rinsed with 0.1M Tris HCl (pH 9.5)-10 mM-$MgCl_2$ and then developed with BCIP-NBT system at room temperature for 20 minutes. The membrane was stored after washing with PBS-0.1% Tween 20.

Figure 2:
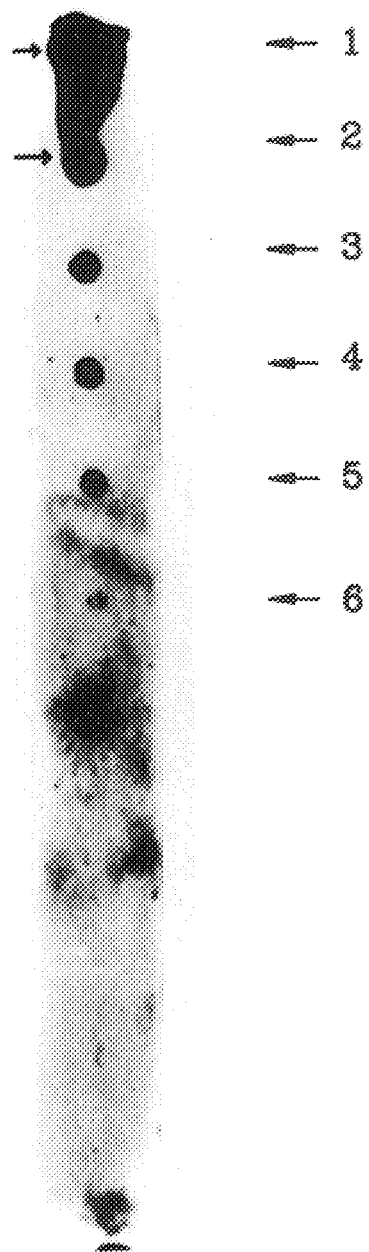
FIG. 2 shows the result of detection of *Escherichia coli* rRNA in Example 1.

Results (i) λDNA or *E. coli* rRNA was dot-spotted and detected by alkaline phosphatase-labeled polyethyleneimine. The results were shown in FIGS. 1 and 2. The amounts of λDNA spots are (1) 4.7 μg, (2) 470 ng, (3) 47 ng, (4) 4.7 ng, (5) 470 pg, (6) 47 pg, (7) 4.7 pg, (8) 470 fg from the top in FIG. 1. The amounts of γRNA spots are (1) 5 μg, (2) 500 ng, (3) 50 ng, (4) 5 ng, (5) 500 pg, (6) 50 pg from the top in FIG. 2.

Figure 3:
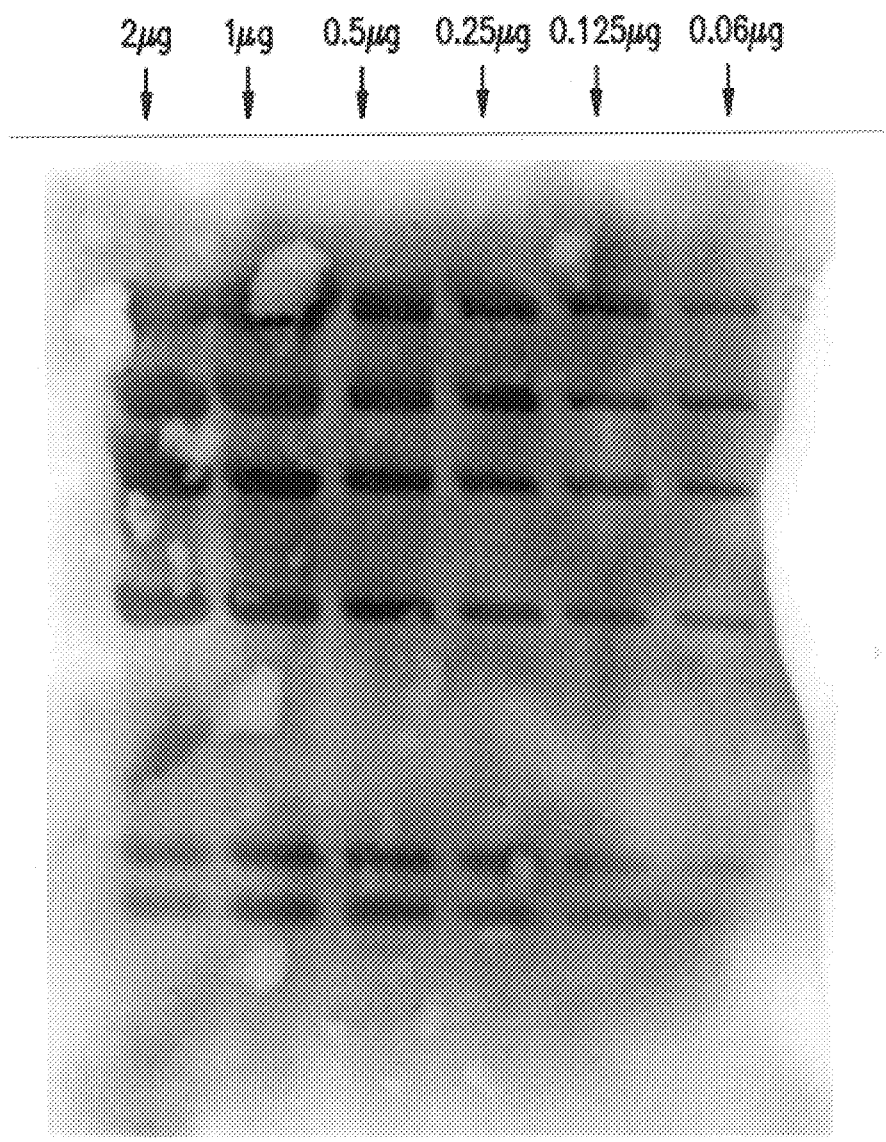
FIG. 3 represents a photograph of electrophoresis of λHind III DNA in Example 1.

(ii) After serial dilutions of λHind III DNA were fractionated by agarose gel electrophoresis, electro-blotted from gel to a membrane, each specimen was detected by alkalinephosphatase-labeled polyethyleneimine. The results were shown in FIG. 3. The results showed that the profile obtained by ethydium bromide after agarose gel electrophoresis is completely identified with the pattern obtained by electroblotting of the specimen of the serial dilution (0.06 μg), and thus proved that the method of the invention is correct.

Figure 4:
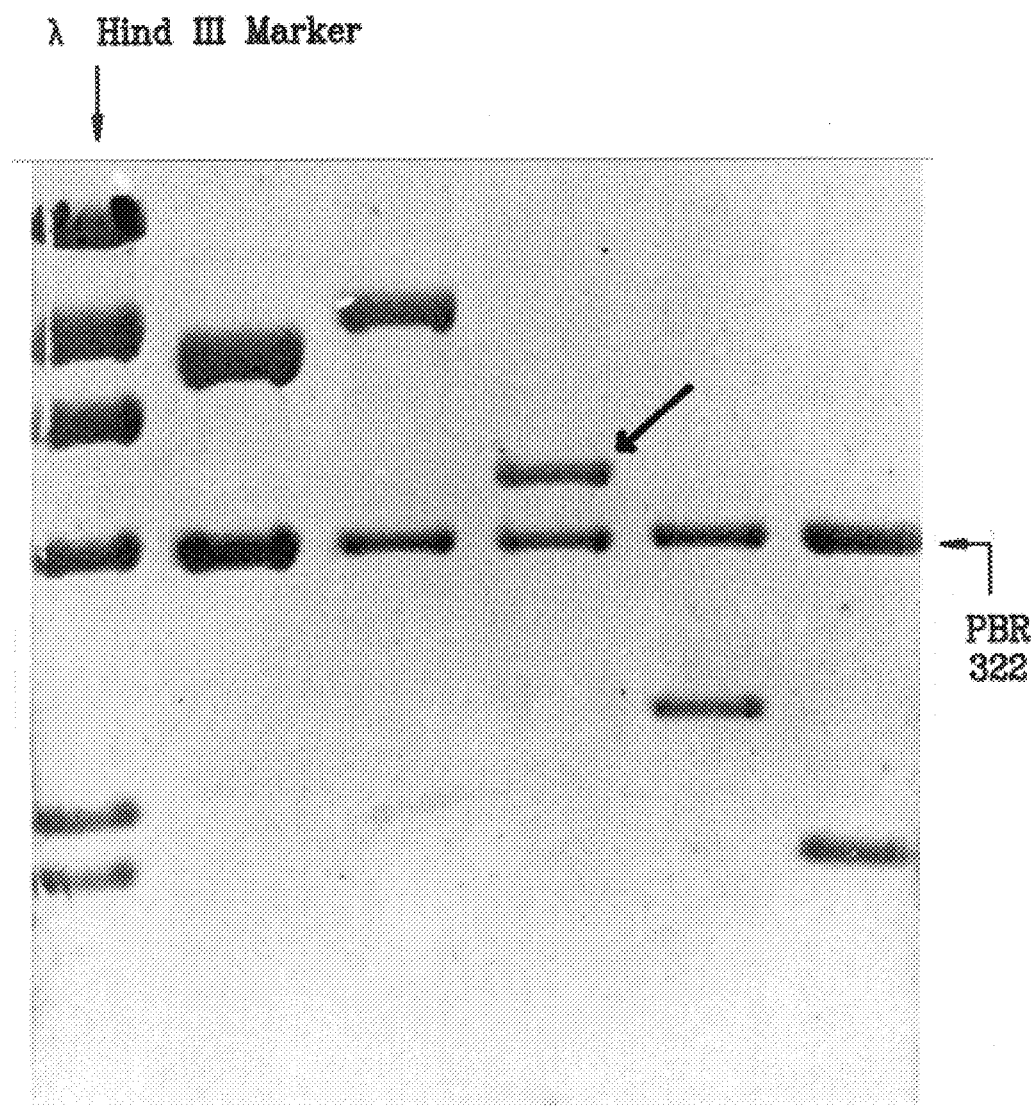
FIG. 4 represents a photograph of electrophoresis showing the result (the color development pattern according to the invention) of splitting DNA fragment inserted into pBR322 with a restriction enzyme.
Figure 5:
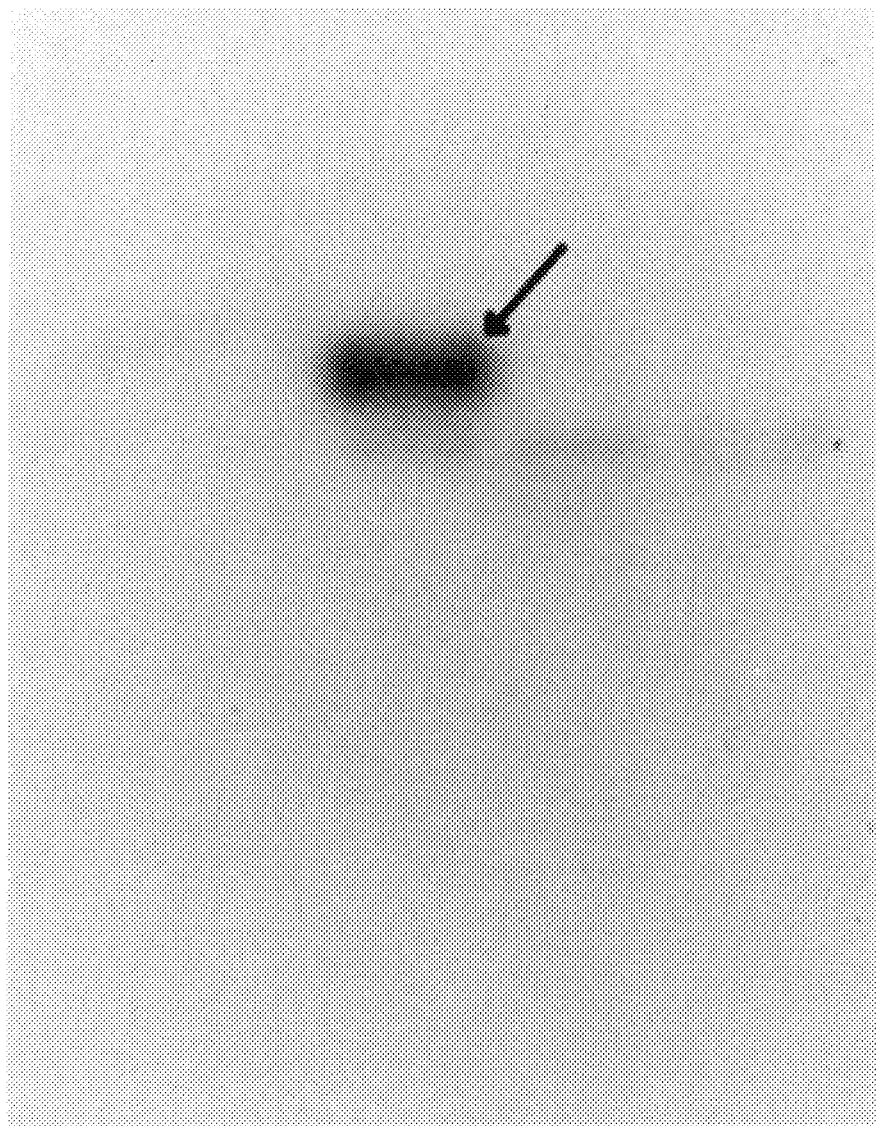
FIG. 5 represents a photograph of electrophoresis showing the result (the X-ray profile) of splitting DNA fragment inserted into pBR322 with a restriction enzyme.

(iii) DNA fragments inserted in pBR322, containing a size marker of λHind III DNA, were split with a restriction enzyme, fractionated by agarose gel electrophoresis, transferred on membrane by electoblotting, and hybridized with $^{32}$P-DNA probe. The membrane was exposed to an X-ray film to obtain signals (FIG. 5). In order to identify a kind of hybridized DNA, the membrane was treated with peroxidase-labeled polyethyleneimine and positions of all blotted DNA were visualized (FIG. 4).

Figure 6:
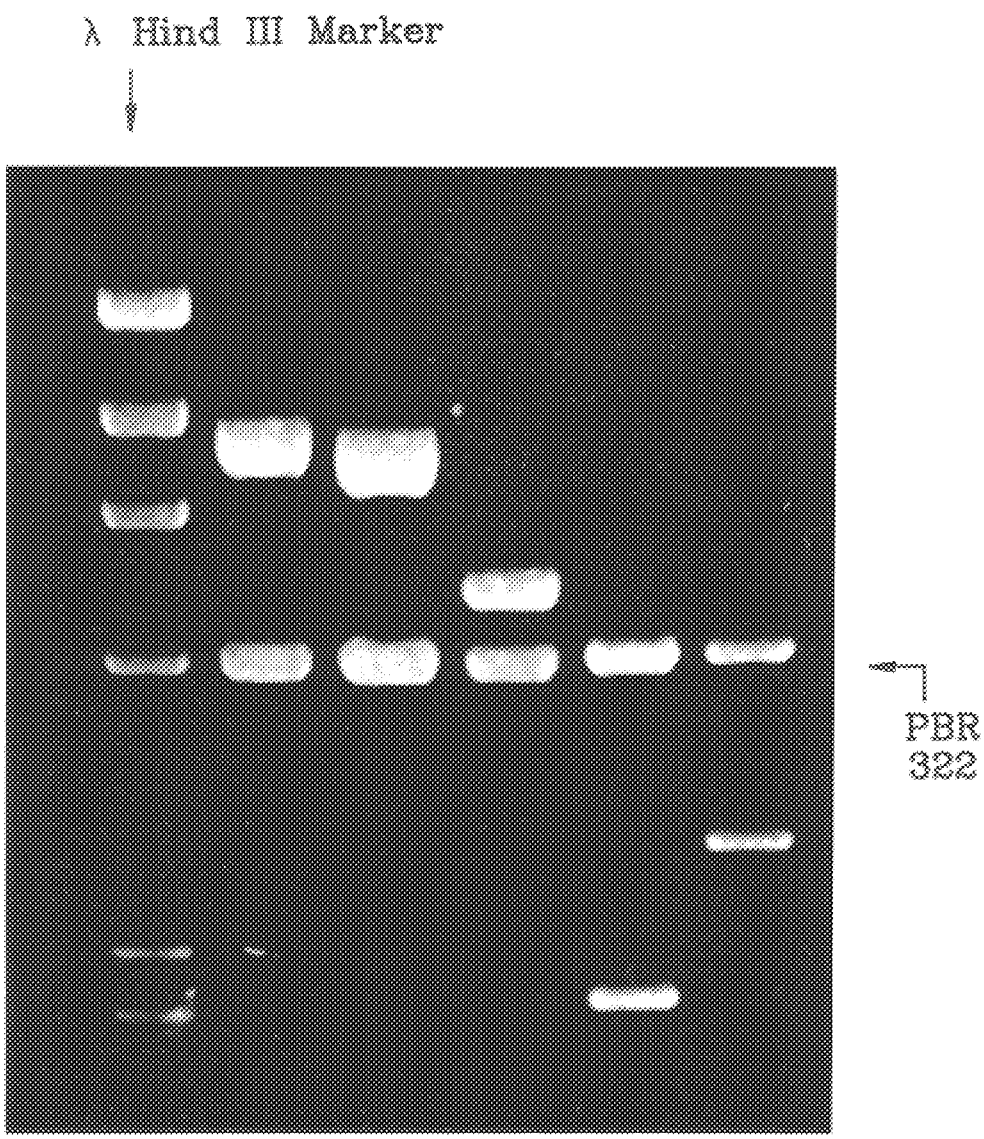
FIG. 6 represents a photograph of electrophoresis of λHind III DNA in Example 1.
Figure 7:
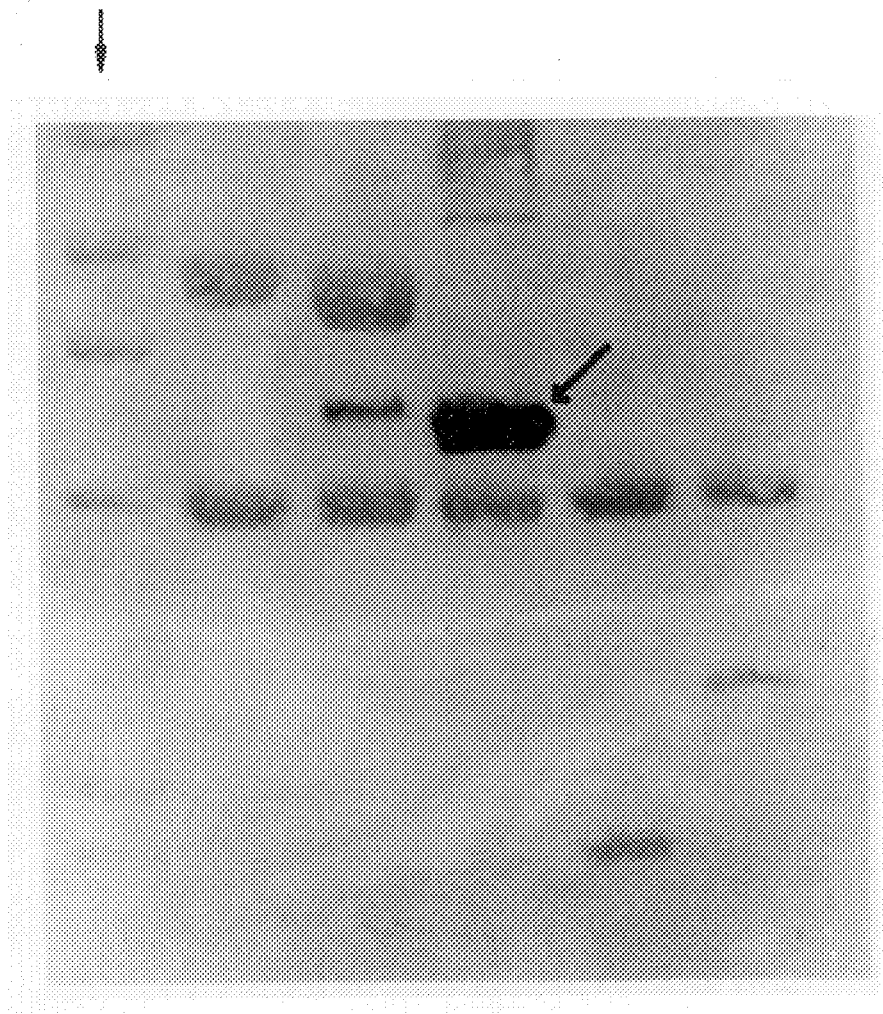
FIG. 7 like FIG. 6 in Example 1 represents the photograph of electrophoresis of λHind III DNA in Example 1.
Figure 8:
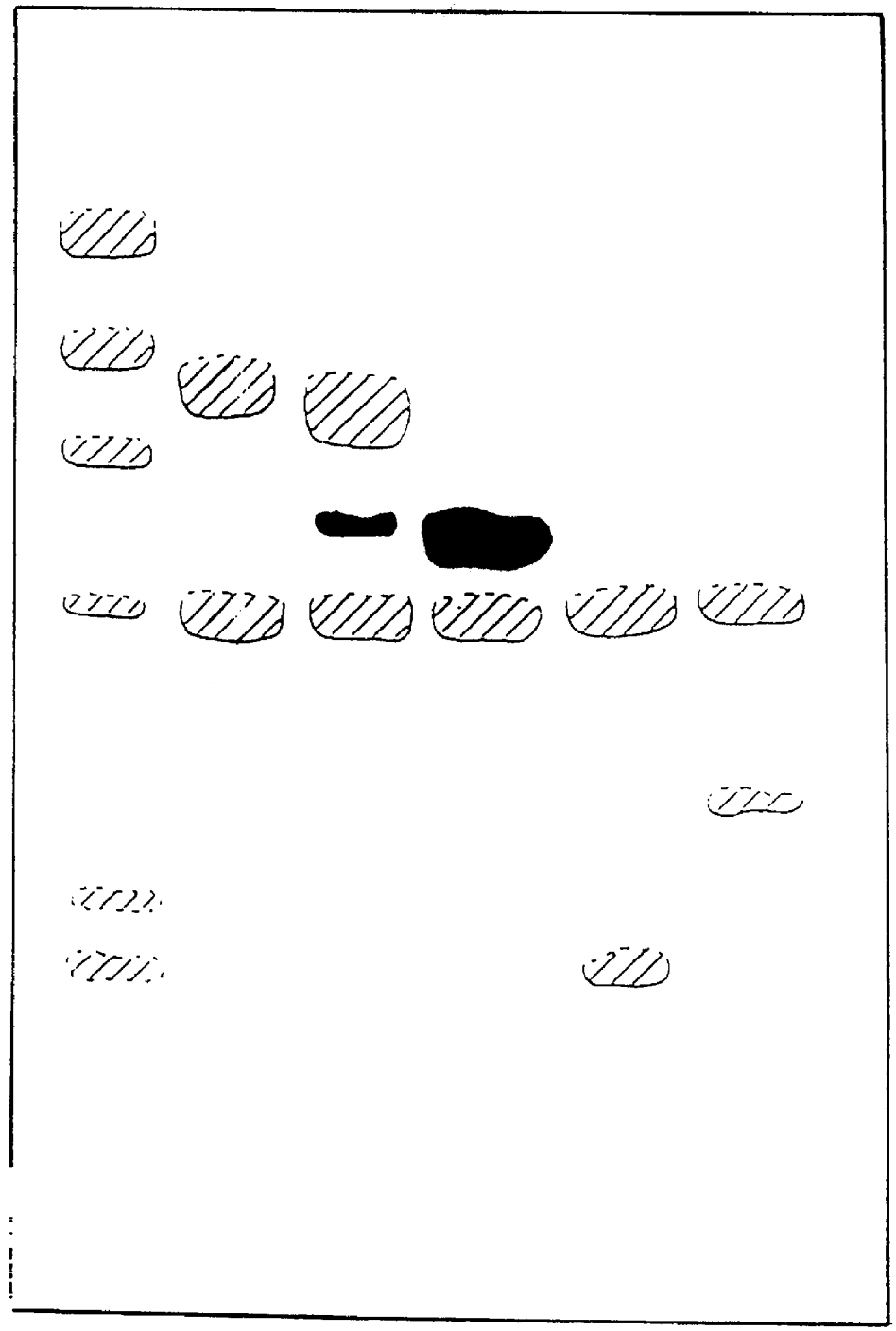
FIG. 8 shows the difference in color in FIG. 7.

(iv) The DNA fragments which were treated as described in step (iii) were hybridized with Bio-DNA probe system to simultaneously detect both of hybridized DNA and non-hybridized DNA. By suitable choice of Bio-DNA probe and each enzyme in alkalinephosphatase-labeled streptavidin and peroxidase-labeled polyethyleneimine, a hybridized DNA and a non-hybridized DNA were differentiated by a double staining system. The results were shown in FIG. 7 and also, the difference in color was shown in FIG. 8. In the figure, the shaded portion represents brown color (the peroxidase-labeled polyethyleneimine system) and the black portion represents purple color. The patterns were identified with the results (FIG. 6) obtained by the ethydium bromide staining after the same treatment as described above.

What is claimed is:

1. A method of detecting a nucleic acid which comprises bringing a membrane suspected to carry or contain a nucleic acid into contact with a polyamine to which a label capable of generating a detectable signal or a precursor thereof is bound, to form an electrostatically bonded complex between said nucleic acid and said polyamine on the membrane, said precursor, if used, converting into said label, removing the polyamine which has not formed any electrostatically bonded complex before or after the conversion of said precursor and then detecting said label to thereby detect the nucleic acid.

2. The method of detecting a nucleic acid according to claim 1, wherein said label capable of generating a detectable signal or a precursor thereof is an enzyme.

3. The method of detecting a nucleic acid according to claim 2, wherein said enzyme is alkaline phosphatase or peroxidase.

4. The method of detecting a nucleic acid according to claim 2 or 3, wherein said enzyme binds to said polyamine through a crosslinking agent.

5. The method of detecting a nucleic acid according to claim 4, wherein said crosslinking agent is benzoquinone.

6. The method of detecting a nucleic acid according to claim 1, wherein said polyamine is a naturally occurring polyamine or a synthetic polyamine, said polyamine, whether naturally occurring or synthetic, having an aliphatic chain of 3 to 50 carbon atoms and primary amino groups at both ends of said chain which may be interrupted by an imino group.

7. The method of detecting a nucleic acid according to claim 6, wherein said polyamine is a polyamine having an aliphatic chain of 6 to 15 carbon atoms.

8. The method of detecting a nucleic acid according to claim 7, wherein said polyamine is a synthetic polyamine.

9. The method of detecting a nucleic acid according to claim 8, wherein said polyamine is polyethyleneimine.

10. A method of distinguishing target nucleic acid from non-target nucleic acid in a nucleic acid sample, which comprises treating said sample nucleic acid immobilized on a membrane with both (i) and (ii) as follows, wherein (i) and (ii) can be performed in voluntary order such that said target nucleic acid in said nucleic acid sample is distinguished from all non-target nucleic acid present on the membrane:

(ii) bringing into contact with the immobilized nucleic acid sample a probe which forms a detectable hybrid with said target nucleic acid and then detecting the detectable hybrid to thereby detect the target nucleic acid, and (ii) bringing into contact with the immobilized nucleic acid sample a polyamine to which a label capable of generating a detectable signal or a precursor thereof is bound, to form an electrostatically bonded complex between all of the sample nucleic acid immobilized on said membrane and said polyamine.

11. The method of distinguishing a nucleic acid according to claim 10, wherein the step (i) is carried out by Southern blot hybridization.

12. The method of distinguishing a nucleic acid according to claim 10, wherein said label capable of generating a detectable signal or a precursor thereof is an enzyme.

13. The method of distinguishing a nucleic acid according to claim 12, wherein said enzyme is alkaline phosphatase or peroxidase.

14. The method of distinguishing a nucleic acid according to claim 13, wherein said enzyme binds to said polyamine through a cross-linking agent.

15. The method of distinguishing a nucleic acid according to claim 14, wherein said cross-linking agent is benzoquinone.

16. The method of distinguishing a nucleic acid according to claim 10 or 14, wherein said polyamine is a naturally occurring polyamine or a synthetic polyamine, said polyamine, whether naturally occurring or synthetic, having an aliphatic chain of 3 to 50 carbon atoms and primary amino groups at both ends of said chain which may be interrupted by an imino group.

17. The method of distinguishing a nucleic acid according to claim 16, wherein said polyamine is a polyamine having an aliphatic chain of 6 to 15 carbon atoms.

18. The method of distinguishing a nucleic acid according to claim 17, wherein said polyamine is a synthetic polyamine.

19. The method of distinguishing a nucleic acid according to claim 18, wherein said polyamine is polyethyleneimine.

20. A kit for detecting a nucleic acid comprising:

(i) an enzyme-labeled polyamine and (ii) a chromogen which generates a label by enzymatic action.

21. The kit for detecting a nucleic acid according to claim 20, wherein said enzyme is alkalinephosphatase or peroxidase.

22. The kit for detecting a nucleic acid according to claim 20, wherein said enzyme binds to said polyamine through a cross-linking agent.

23. The kit for detecting a nucleic acid according to claim 22, wherein said cross-linking agent is benzoquinone.

24. The kit for detecting a nucleic acid according to claim 20 or 22, wherein said polyamine is a naturally occurring polyamine or a synthetic polyamine, said polyamine whether naturally occurring or synthetic, having an aliphatic chain of 3 to 50 carbon atoms and primary amino groups at both ends of said chain which may be interrupted by an imino group.

25. The kit for detecting a nucleic acid according to claim 24, wherein said polyamine is a polyamine having an aliphatic chain of 6 to 15 carbon atoms.

26. The kit for detecting a nucleic acid according to claim 25, wherein said polyamine is a synthetic polyamine.

27. The kit for detecting a nucleic acid according to claim 26, wherein said polyamine is polyethyleneimine.

* * * * *

UNITED STATES PATENT AND TRADEMARK OFFICE
CERTIFICATE OF CORRECTION

PATENT NO. : 5,824,474
DATED : Oct. 20, 1998
INVENTOR(S) : Akio Matsuhisa, et al.

It is certified that error appears in the above-identified patent and that said Letters Patent is hereby corrected as shown below:

On the title page, under [87], change the "PCT Pub. Date" to --Feb. 16, 1995--.

Signed and Sealed this

Second Day of February, 1999

Attest:

Attesting Officer

*Acting Commissioner of Patents and Trademarks*